United States Patent
Khambay et al.

[11] Patent Number: 5,886,027
[45] Date of Patent: Mar. 23, 1999

[54] FUNGICIDAL COMPOUNDS

[75] Inventors: Bhupinder Pall Singh Khambay, Southall; Duncan Batty, Kempston, both of England

[73] Assignee: BTG International Limited, London, England

[21] Appl. No.: 66,973

[22] Filed: Apr. 28, 1998

Related U.S. Application Data

[63] Continuation of PCT/GB96/02621, Oct. 28, 1996 published as WO97/16970, May 15, 1997.

[30] Foreign Application Priority Data

Nov. 9, 1995 [GB] United Kingdom ............... 9522996

[51] Int. Cl.⁶ .................................................. A61K 31/35
[52] U.S. Cl. ............................................................. 514/454
[58] Field of Search .............................................. 514/454

[56] References Cited

U.S. PATENT DOCUMENTS 4,929,642  5/1990  Linder et al. ........................... 514/510
4,970,328  11/1990  Lindner et al. ......................... 552/298

FOREIGN PATENT DOCUMENTS 413 224 A1  8/1990  European Pat. Off. .
WO 95/32176  11/1995  WIPO .

OTHER PUBLICATIONS

Caplus Abstract 1983:50453, Inoue et al., J. Chem. Soc., Chem. Commun. (17), pp. 993–994, 1982.
Caplus Abstract 99:155150, Inoue et al., Phytochemistry, 22(3) pp. 737–741, 1983.
Bios, Biotech. Biochem., 59 (10) (1995(, pp. 1999–2000—"Synthesis of an Antifungal Naphthoquinone Isolated from Rhinacanthus nasutus (Acanthaceae)".
Phytochemistry, vol. 22, N° 3, (1983) pp. 737–741—"Quinones of Streptocarpus Dunnii".
A Matthey et al., Liebigs Ann. Chem. (1980), pp. 779–785—"1,2–Naphthochinon–Derivate aus Kulturen des Mycosymbionten der Flechte Trypethelium eluteriae (Trypetheliaceae)".

*Primary Examiner*—Raymond Henley, III
*Attorney, Agent, or Firm*—Nixon & Vanderhye

[57] ABSTRACT

A method of controlling or preventing fungal infestation which comprises treating a locus subject to attack with dunnione of formula (I). Fungicidal compositions containing dunnione are also provided.

12 Claims, No Drawings

FUNGICIDAL COMPOUNDS

This is a continuation of PCT application PCT/GB96/02621, filed 28 Oct. 1996, published as WO97/16970, May 15, 1997.

This invention relates to the use of dunnione as a fungicide and processes for the preparation of compositions containing dunnione suitable for such use.

The ability of fungi to develop resistance to fungicidal agents means that there is an ongoing need for new agents for their control. It is known that certain napthoquinones and their derivatives have fungicidal activity eg U.S. Pat. No. 4,970,328 and U.S. Pat. No. 4,929,642. Furanyl derivatives, (A) and (B), of 1,4-Napthoquinones with one or two alkyl substituents at the carbon ortho- to the furanyl oxygen were prepared and investigated by Jacobsen and Wengel (Pestic. Sci., 1986, 17, 686–690). The dialkyl derivative (B) was found to have intermediate fungicidal activity and the mono-alkylated derivative (A) was inactive; it is apparent that both these compounds are not as fungicidally active as some of the non-furanyl compounds investigated by Jacobsen and Wengel.

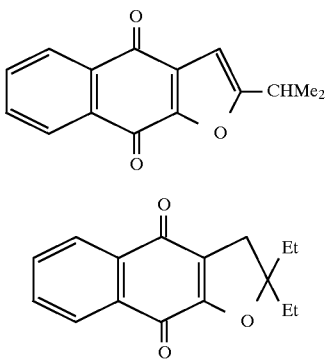

The present inventors have now determined that a naturally occurring fungicidal derivative of napthoquinone, dunnione, may be used as a fungicidal agent having superior fungicidal activity, especially against strains resistant to presently used agents. The attendant advantages of a naturally occurring agent include natural product sourcing and a potentially safer product.

A first aspect of the present invention provides the use of dunnione as a fungicidal agent. The structure of dunnione is given as formula I. It should also be appreciated that dunnione is capable of existing as different enantiomers and the invention includes both the individual enantiomers and mixtures of such enantiomers. Dunnione may be extracted from the aerial parts of the plants *Streptocarpus dunnii* or *Calceolaria Integrifolia* or prepared from either II or III by acid catalysed cyclisation reactions. III is formed from IV using an aqueous solution of methanol and potassium hydroxide.

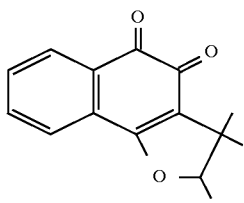

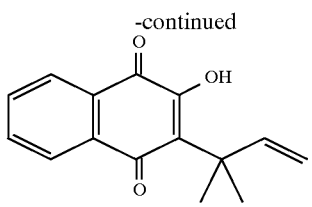

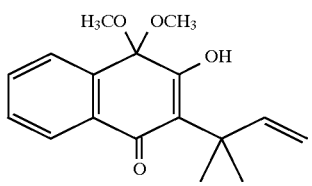

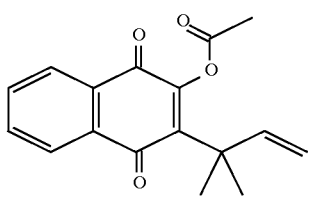

A second aspect of the invention provides a fungicidal composition which comprises a carrier and, as active ingredient, dunnione. This aspect necessarily includes a method of making such a composition by bringing dunnione into association with at least one carrier. It is also envisaged that different enantiomers or mixtures of enantiomers of dunnione may have different levels or spectra of activity and thus compositions may comprise individual enantiomers or mixtures of enantiomers.

The compositions of the invention may contain from 0.0001 to 0.1% by weight of the active ingredient of formula I. Preferably the compositions contain from 0.0002 to 0.075% by weight of the active ingredient when they are in ready-to-use form. However, higher concentrations, for instance, up to 95%, may be present in compositions to be sold as concentrates for dilution before use.

To prepare the compositions of the invention dunnione may be mixed with a variety of appropriate inert carriers such as solvents, diluents and/or surface-active agents to form dusts, granular solids, wettable powders or other solid preparations or emulsions, emulsifiable concentrates, sprays, aerosols or other liquid preparations. Suitable solvents and diluents include water, aliphatic and aromatic hydrocarbons such as xylene or other petroleum fractions and alcohols such as ethanol. Surface-active agents may be of an anionic, cationic or non-ionic type. Anti-oxidants or other stabilisers may also be included as well as perfumes and colourings. These inert carriers may be of the type and in proportions such as are conventionally used in fungicidal compositions.

In addition to these inert carriers, the compositions of the invention may also contain one or more further active ingredients. These further active ingredients may be other compounds which exhibit fungicidal activity and these other compounds may exhibit a synergistic effect with the compounds of the present invention.

A third aspect of the invention provides a method of combatting fungal pests comprising treating a locus subject to attack by said fungal pests with dunnione or a composition as defined above. Preferably, the locus comprises the fungus or fungi per se or environments subject to or subjected to attack by these.

The invention is further illustrated by the following examples.

EXAMPLE 1

Preparation of Dunnione

The preparation of dunnione has been described by Cooke, (Nature, (1948), 163, 178). 2-[1,1-dimethyl-2-propenyl]-3-hydroxy-1,4-napthoquinone (500 mg, 2.06 mmol) prepared according to WO 95/32176 was dissolved in concentrated sulphuric acid (10 ml), stirred for 10 minutes at room temperature and poured onto ice in water (100 ml). The aqueous mixture was extracted with ether (3×50 ml) and the combined ether layers were washed with water (2×50 ml), saturated sodium chloride (50 ml) and dried over magnesium sulphate. Filtration of the resulting solution, removal of the solvent by evaporation and recrystallisation of the product from petroleum ether (60°–80° C.) yielded dunnione (476 mg) as orange-red needles, mp 98°–99° C.

EXAMPLE 2

Extraction of Dunnione

The extraction of dunnione from *Calceolaria Integrifolia* was carried out according to the method of Rüedi and Evgster (Helvetica Chimica Acta, 60, 945–947, (1977)). Extraction of dunnione from *streptocarpus dunnii* was carried out according to the method of Price and Robinson (J. Chem. Soc., (1939), 1522).

EXAMPLES 3 and 4

Determination of the Anti-Fungal Activity of Dunnione

The anti-fungal activity of dunnione on fungi grown under in vitro conditions and on 14 day old seedlings was investigated. The species investigated in Example 3 were *Septoria tritici* (wheat leaf blotch), *Rhynchosporium secalis* (barley leaf blotch), *Ustilago maydis* (maize smut), *Neurospora crassa*, *Botrytis cinerea* (grey mould), *Fusarium graminearum*, *Pseudocercosporella herpotrichoides* (eyespot) and *Erysiphe graminis* f.sp *hordei* (powdery mildew). The effects that the dosage levels of the compounds under investigation had on the colony size of the above mentioned species was observed and conclusions were drawn regarding their anti-fungal activities.

EXAMPLE 3

In Vitro Assays

Fungal colonies were incubated and grown on potato dextrose agar (PDA), which was prepared from stock solutions (20 mg ml$^{-1}$) in ethanol:acetone (1:1), autoclaved and treated with the compound under investigation. A four fold dilution series was prepared for each compound with doses ranging from 20 $\mu$g ml$^{-1}$ to 0.08 $\mu$g ml$^{-1}$. For fungi which grow only as yeast-like colonies the growth was measured as the Minimum Inhibitory Concentration (MIC); for other species the growth was measured as colony diameter and the Effective Dose$_{50}$ (ED$_{50}$) values were calculated from the dose response relationship. In one series of experiments Czapek-Dox plus mycological peptone (1% w/v CDM) was used instead of PDA. Each fungus was incubated at the optimum temperature for their growth. The anti-fungal activity of dunnione was compared with that of known anti-fungal compounds as a control. The results, shown in Tables 1(a) to (g) below indicate that the anti-fungal activity of the compound tested was dependent on the nature of the fungal strains used. dunnione was active against *Septoria tritici*, *Rhynchosporium secalis* and *Ustilago maydis*; the levels of activity against these pathogens were similar, or better, than the azole fungicides currently in use. It also exhibited some activity against *Botrytis cinerea* and *Fusarium graminearum*; these two pathogens are difficult to control using existing azole fungicides. Significant activity against *Neurospora crassa* was observed.

TABLE 1(a)

*Septoria tritici*

| Isolate | Sensitivity MIC ($\mu$g/ml) | |
| --- | --- | --- |
| | Flutrifol | dunnione |
| S27 | 40 | 5 |
| RL2 | 1 | 5 |

TABLE 1(b)

*Rhynchosporium secalis*

| Isolate | Sensitivity MIC ($\mu$g/ml) | | | |
| --- | --- | --- | --- | --- |
| | Carbendazim | Triadimenol | Propiconazole | dunnione |
| CDM agar | | | | |
| 81 | 0.1 | >50 | 2.0 | 5 |
| 86 | 0.1 | 3.2 | 0.4 | >5 |
| 97 | 0.1 | >50 | >10 | 5 |
| 101 | 0.1 | >50 | >10 | >5 |
| 110 | 0.1 | >50 | 2.0 | >5 |
| 115 | 0.1 | 1.6 | 0.08 | 20 |
| 117 | 0.1 | 12.5 | 2.0 | 5 |
| 118 | 0.1 | >50 | >10 | 20 |
| 120 | 100 | >50 | >10 | 20 |
| PDA | | | | |
| 810 | 0.1 | >50 | >10 | 20 |

TABLE 1(c)

*Ustilago maydis*

| Isolate | ED$_{50}$ ($\mu$g/ml) dunnione |
| --- | --- |
| ATCC-14826 wild-type | 3.0 |

TABLE 1(d)

*Neurospora crassa*

| Isolate | ED$_{50}$ ($\mu$g/ml) dunnione |
| --- | --- |
| Am 132a | 2 |

TABLE 1(e)

*Botrytis cinerea*

| Isolate | Dicarboximide | Benzimidazole | Sensitivity ED$_{50}$ ($\mu$g/ml) dunnione |
| --- | --- | --- | --- |
| R3B6 | R | R | >20 |
| RW10 | S | S | >20 |

S = Susceptible; R = Resistant

TABLE 1(f)

*Fusarium graminearum*

| Isolate | Benzimidazole | Sensitivity $ED_{50}$ ($\mu$g/ml) dunnione |
|---|---|---|
| JF18 | R | 20 |

R = Resistant

TABLE 1(g)

*Pseudocercosporella herpotrichoides*

| Isolate | Benzimidazole | Sensitivity $ED_{50}$ ($\mu$g/ml) dunnione |
|---|---|---|
| CR03A | R | 17 |

R = Resistant

EXAMPLE 4

Further In Vitro Assays

The fungicidal activity of dunnione to isolates of *Aspergillus niger*, *Pyricularia oryzae* and *Rhizoctonia solani* was tested using the procedure described in Example 3. Each fungus was tested on agar in four petri dishes per treatment, with three replicate fungal colonies per plate (one for *R. solani*). *A. niger* and *R. solani* were incubated for 4 days at 20°–25° C.; *P.oryzae* was incubated for 7 days. Increase in colony diameter was then used to measure colony activity.

Dunnione was also tested on four isolates of *Pseudocercosporella herpotrichoides;* two slow growing R-types and two faster growing W-type isolates. One isolate of each type was sensitive to fungicides such as carbendazim and prochloraz and the other was fully resistant. Colony diameters were measured after two weeks at 20° C.

Dunnione was also tested against four isolates of the potato tuber pathogens *Helminthosporium solani* and *Fusarium sulphureum*. Two isolates of each were sensitive to the fungicide thiabendazole (TBZ) and two had some degree of resistance. The same procedures as those used for *P. herpotrichoides* were followed except that the replicates were grown on malt extract agar and growth was measured on two occasions.

The results, shown in Tables 2(a) to 2(f) below, indicate that dunnione is active against *Aspergillus niger*, *Pyricularia oryzae* and *Rhizoctonia solani*. Its activity against *Pseudocercosporella herpotrichoides* was inconsistent. There was no evidence of cross-resistance with carbendazim (Table 2(d)) or with thiabendazole in *H. solani* or *F. sulphureum* (Tables 2(e) and (f)).

TABLE 2(a)

Activity of dunnione against *Aspergillus niger*

| | % inhibition of growth in colony diameter | | | |
|---|---|---|---|---|
| Compound | 100 mg/l | 20 mg/l | 4 mg/l | 1 mg/l |
| dunnione | 100 | 99 | 30 | |
| Prochloraz | | | | 97.1 |

TABLE 2(b)

Activity of dunnione against *Pyricularia oryzae*

| | % inhibition of growth in colony diameter | | | |
|---|---|---|---|---|
| Compound | 100 mg/l | 20 mg/l | 4 mg/l | 1 mg/l |
| dunnione | 100 | 99 | 75 | |
| Carbendazim | | | 99.4 | 14.7 |

TABLE 2(c)

Activity of dunnione against *Rhizoctonia solani*

| | % inhibition of growth in colony diameter | | | |
|---|---|---|---|---|
| Compound | 100 mg/l | 20 mg/l | 4 mg/l | 1 mg/l |
| dunnione | 100 | 93 | 37 | |
| Carbendazim | | | 81.2 | 3.3 |

TABLE 2(d)

Activity of dunnione against W-type and R-type isolates of *Pseudocercosporella herpotrichoides*

| | Sensitivity to | Activity at 5 mg/l | |
|---|---|---|---|
| Fungus Type | Carbendazim | Carbendazim | dunnione |
| W-type | Sensitive | 100 | 50 |
| W-type | Resistant | 5 | 30 |
| R-type | Sensitive | 100 | −15 |
| R-type | Resistant | −14 | 4 |

TABLE 2(e)

Activity of dunnione against isolates of *Helminthosporium solani* with different levels of resistance to thiabendazole (TBZ)

| | Activity at 5 mg/l | | | |
|---|---|---|---|---|
| | 8 days | | 14 days | |
| Isolate | TBZ | dunnione | TBZ | dunnione |
| S1 | 100 | 65 | 100 | 53 |
| S2 | 100 | 63 | 100 | 86 |
| R1 | 43 | 57 | 20 | 87 |
| R2 | 100 | 70 | 100 | 56 |

S1, S2 = isolates sensitive to TBZ; R1, R2 = isolates resistant to TBZ.

TABLE 2(f)

Activity of dunnione against isolates of *Fusarium sulphureum* with different levels of resistance to thiabendazole

| | Activity at 5 mg/l | | | |
|---|---|---|---|---|
| | 8 days | | 14 days | |
| Isolate | TBZ | dunnione | TBZ | dunnione |
| S1 | 100 | 22 | 100 | nd |
| S2 | 100 | 11 | 100 | 5 |
| R1 | 60 | 4 | 64 | 6 |
| R2 | 70 | 16 | 70 | 12 |

S1, S2 = isolates sensitive to TBZ; R1, R2 = isolates resistant to TBZ.
nd = no data; the fungal colonies on the control medium had reached the edges of the culture plates

EXAMPLE 5

14 Day Old Seedlings 14 day old seedlings were sprayed to run off 24 hours prior to inoculation with *conidia* of *Erysiphe graminis* f.sp *hordei*. Solutions of dunnione, prepared in dilute Tween 20 solutions (1 drop Tween 20 per 100 ml water), were sprayed onto the seedlings; the final concentrations of the dunnione in the solutions used were 0.75 mg ml$^{-1}$ and 0.075 mg ml$^-$1, the former being equivalent to the field application rate of a triazole fungicide. Control seedlings were sprayed with a solution of Tween 20 only. The growth of barley powdery mildew was assessed 7 days after inoculation as a percentage of leaf area infected. The results shown in Table 3 indicate that dosage levels below those currently used for triazole fungicides are fungicidally effective and produce no noticeable phytotoxic effects. It may be preferred to use concentrations of less than 0.75 mg ml$^{-1}$ when treating certain species of plant as higher concentrations may induce some phytotoxic effects.

TABLE 3

Effect of dunnione on the Growth of *Erysiphe graminis* f.sp *horedi*

| Isolate | Triadimenol | % Disease Control dunnione mg/ml | |
| --- | --- | --- | --- |
| | | 0.75 | 0.075 |
| 23D5 | S | 100 | 45 |
| 212 | R | 100 | 50 |

S = Sensitive; R = Resistant

We claim:

1. A method of controlling or preventing fungal infestation which comprises treating a locus subject to attack with dunnione of formula (I)

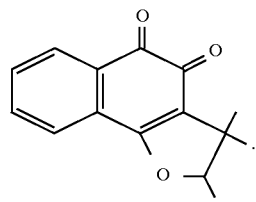

2. A method according to claim 1, in which dunnione is in the form of an enantiomer or a mixture of enantiomers.

3. A method according to claim 1, in which dunnione is in the form of a plant extract.

4. A method according to claim 3, in which the extract is obtainable from *Streptocarpus dunnii* or *Calceolaria integrifolia*.

5. A composition comprising dunnione, an inert carrier and a stabiliser.

6. A composition according to claim 5, further comprising a surface-active agent.

7. A composition according to claim 5, in which the composition is in the form of a solid formulation.

8. A composition according to claim 5, in which the composition is in the form of a dust, granular solid, wettable powder, emulsion, emulsifiable concentrate, spray or aerosol.

9. A composition according to claim 5, which further comprises one or more additional fungicidally active ingredients.

10. A method of preparing a fungicidal composition which comprises the steps of admixing dunnione with an appropriate carrier such as to produce a composition as claimed in claim 5.

11. A material treated with dunnione in accordance with claim 1.

12. A material as claimed in claim 11 being a plant material.

* * * * *